US006245752B1

(12) United States Patent
Barbera-Guillem et al.

(10) Patent No.: US 6,245,752 B1
(45) Date of Patent: Jun. 12, 2001

(54) COMPOSITIONS AND METHODS FOR TOLERIZATION IN IMMUNE COMPLEX-MEDIATED DISEASE PROGRESSION

(75) Inventors: Emilio Barbera-Guillem, Powell; M. Bud Nelson, Worthington, both of OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/299,289

(22) Filed: Apr. 26, 1999

Related U.S. Application Data

(60) Provisional application No. 60/083,155, filed on Apr. 27, 1998.

(51) Int. Cl.[7] .................................................. A61K 31/715

(52) U.S. Cl. .................................. 514/54; 514/2; 514/53; 514/61; 424/181.1; 424/184.1; 424/185.1; 424/193.1; 424/194.11; 424/195.11; 424/204; 424/278.1; 424/279.1; 424/280.1; 424/282.1

(58) Field of Search ............................. 424/181.1, 184.1, 424/185.1, 193.1, 194.11, 195.11, 197.11, 204, 278.1, 279.1, 280.1, 282.1; 514/2, 53, 54, 61

(56) References Cited

U.S. PATENT DOCUMENTS

| | | | | |
|---|---|---|---|---|
| 4,663,049 | * | 5/1987 | Kolff et al. | 210/641 |
| 5,126,131 | | 6/1992 | Dintzis et al. | 424/193.1 |
| 5,268,454 | | 12/1993 | Barstad et al. | 424/193.1 |
| 5,276,013 | | 1/1994 | Conrad et al. | 514/2 |
| 5,833,990 | * | 11/1998 | Heerze et al. | 424/185.1 |
| 6,060,056 | * | 5/2000 | Coutts et al. | 424/184.1 |

OTHER PUBLICATIONS

Dintzis et al., Studies on the immunogenicity and tolerogenicity of T–independent antigens, Journal of Immunology, Nov. 1983, vol. 131:2196–2203.

Dintzis et al., "The immunogenicity of soluble of haptenated polymers is determined by molecular mass and hapten valence", Journal of Immunology, Aug. 1989, vol. 143:1239–1244.

Dintzis et al., "Inhibition of antibody formation by receptor cross–linking: the molecular characteristics of inhibitory haptenated polymers", European Journal of Immunology, 1990, vol. 20:229–232. Month Not Available.

Dintzis et al., "Inhibition of anti–DNP antibody formation by high doses of DNP–Polyacrylamide molecules: effects of hapten density and hapten valence", Journal of Immunology, Jul. 1985, vol. 135:423–427.

Dintzis and Dintzis, "Profound specific suppression by antigen of persistent IgM, IgG, IgE antibody production", Proceedings of the National Academy of Sciences, USA, Feb. 1992, vol 89:1113–1117.

* cited by examiner

*Primary Examiner*—Kathleen K. Fonda
(74) *Attorney, Agent, or Firm*—M. Bud Nelson

(57) ABSTRACT

Methods and compositions are provided for tolerizing shed antigen-specific B cells involved in an immune complex-mediated disease progression. The composition comprises a substantially non-immunogenic carrier molecule to which is linked carbohydrate chains containing a suppressive amount of a repeated, antigenic carbohydrate determinant derived from a shed antigen of interest. In a method of tolerizing shed antigen-specific B cells involved in an immune complex-mediated disease progression, administered to an individual is a therapeutically effective amount of the composition which, when contacting the shed antigen-specific B cells, induces tolerization of the shed antigen-specific B cells.

23 Claims, 4 Drawing Sheets

COMPOSITIONS AND METHODS FOR TOLERIZATION IN IMMUNE COMPLEX-MEDIATED DISEASE PROGRESSION

This is a nonprovisional application based on earlier co-pending provisional application Ser. No. 60/083,155 filed Apr. 27, 1998, which is herein incorporated by reference.

FIELD OF THE INVENTION

The present invention is related to novel compositions and methods for tolerization of specific B lymphocytes in humans. More particularly, the present invention is related to compositions comprising a suppressive amount of a repeated, antigenic carbohydrate determinant linked to a carrier molecule; and methods for using the compositions to tolerize shed antigen-specific B lymphocytes involved in immune complex-mediated disease progression.

BACKGROUND OF THE INVENTION

1. Pathology of the Immune Response in Lymphatic Tissues

Peripheral lymphatic tissues ("lymphoid tissues") provide the environment for generation of a specific immune response to certain antigens when the lymphoid tissues are extra-regional to or draining a principal source of the antigen. In particular, cellular proliferation in lymphoid tissues has been noted in certain pathological conditions including solid, non-lymphoid tumors, and Leishmaniasis.

1.1 Solid, non-lymphoid tumors

The response of an individual to tumor cells involves the reactions and counteractions mediated by both cellular and humoral arms of the immune system. Tumor cell growth may represent a disturbance in the equilibrium of the immune system that is pre-existing, and/or induced by the tumor cells themselves. However, most investigations to date have focused on the role of T cells in tumor immunity. The role of B cells in a tumor-bearing individual still remains unclear. Previous studies have shown that lymph nodes and other lymphoid tissues extra-regional to a primary solid non-lymphoid tumor in cancer patients, and in vivo experimental animal models of tumor development, can undergo a prominent cellular expansion in the germinal centers of the tissue (see, e.g., Eremin et al., 1980, *Br. J. Cancer* 41:62; Bertschmann et al., 1984, *Br. J. Cancer* 49:477–484). Such lymphoid tissues contain immune cells that include B lymphocytes (B cells). However, the reason(s) for this observed B cell proliferative response remains unclear, and has been hypothesized be due to either activation and stimulation directly by tumor cells, and/or indirectly by stimulation of T-helper cells which then activate and stimulate B cells.

Such B cells appear to be able to elicit anti-tumor immunity. In that regard, there are numerous reports that cancer patients have circulating antitumor antibodies (see, e.g., Carey et al., 1976, *Proc. Natl. Acad. Sci. USA* 73:3278–3282; Abe et al., 1989, *Cancer Res.* 80:271–276; Christensen et al., 1989, *Int. J. Cancer* 37:683–688). Thus, it appears that a humoral immune response towards tumor-associated antigens can be mounted in cancer patients. However, the roles of B cells, tumor associated antigens, and lymphoid tissues containing B cells, in the host response to tumor remain poorly defined.

1.2 Leishmaniasis

Protozoans of the genus Leishmania comprise a number of species causing disease (Leishmaniasis) in humans and animals; and hence, is considered a major health problem worldwide. The symptoms and sequelae of the disease depend on several factors relating to the infecting species and host resistance. For example, leishmanial infections range in severity from self-healing, localized cutaneous lesions, to a disseminating, highly destructive mucosal disease. Disseminated disease is ultimately lethal, and is characterized by hepatosplenomegaly, fever, wasting, and pancytopenia. Currently, it is believed that CD4+ T cells are responsible for both the protective immune response as well as the disease promoting immune response observed in individuals infected with a Leishmania species (see, e.g., Bogdan et al., 1990, *Eur. J. Immunol.* 20:2533–2540). The outcome of the infection is determined, at least in part, by the balance of Th1 cells and Th2 cells, wherein a Th1response is host protective, and a Th2 response can lead to disease exacerbation (Liew et al., 1990, *J. Exp. Med.* 172:1359–65). The mechanism by which Th2 cells exacerbate disease is thought to be Th2 cell secretion of IL-4 which neutralizes the macrophage-activating function of interferon-gamma produced by Th1 cells (Liew et al., 1990, supra). Thus, most investigations to date have focused on the role of T cells in immunity to Leishamania species. The role of B cells in an infected individual still remains unclear. However, it is known that the humoral immune response during an infection is characterized by high levels of parasite-specific and non-parasite directed antibodies, with the latter being a result of polyclonal B-cell activation (Evans et al., 1988, *Infect. Immun.* 56:3139–44).

Previous studies have shown that lymph nodes and other lymphoid tissues draining the site of a Leishmania infection are believed to be the principal site for the development of the parasite-specific cellular immune response (Laskay et al., 1997, *J. Immunol.* 158:1246–53). In a study of draining lymph nodes from 8 patients infected with Leishmania major, all such lymph nodes showed mild to marked cellular proliferation with active germinal centers. While only 1 lymph node was seen to contain the parasite (in the amastigote form), all lymph nodes contained a wide distribution of leishmanial antigen, most commonly seen associated with dendritic cells in the interfollicular zone, germinal center, paracortex, and marginal sinus (Al-Gindan et al., 1989, *Int. J. Dermatol.* 28:248–254). These leish-manial containing-lymphoid tissues also contain immune cells that include B lymphocytes (B cells) and plasma cells. However, the roles of B cells, leishmanial antigens, and lymphoid tissues, in the host response to leishmanial infection remain poorly defined.

2. Immunologic Tolerance

Immunologic tolerance is an actively induced unresponsiveness to a specific antigen as the result of antigen-induced functional inactivation or death of lympho-cytes specific for that antigen. Antigens that induce such tolerance are termed "tolerogens", so as to be distinguished from immunogens which are antigens that generate immune responses. Much more is known about the induction of tolerance of CD4+ T cells than in other lymphocytes such as B cells. One mechanism of B cell tolerance and failure to produce antibodies involves interaction of antigens with specific B cells, the first step in B cell activation, in the absence of stimulation by helper T cells or other antigen presenting cells (the second step in B cell activation). Other mechanisms of B cell tolerance have been proposed. B cells can become anergic due to a block in surface immunoglobulin-mediated signaling ("antigen-competition"), in absence of T cell help. Additionally, in absence of co-stimulation by an antigen presenting cell, strong crosslinking of B cell surface immunoglobulins by antigen can induce apoptotic death of normal, mature B cells, but may not induce apoptosis in B cells that produce autoimmune antibodies (see, e.g., Tsubata et al., 1994, *Curr. Biol.* 4:8–17).

Various compounds employed in the development of compositions for inducing humoral anergy to self-antigens (e.g. as encountered in autoimmune diseases such as systemic lupus erythematosus or myasthenia gravis) or allergens are known in the art (see, e.g., U.S. Pat. Nos. 5,126,131, 5,276,013, 5,268,454, the disclosures of which are herein incorporated by reference). Briefly, substantially non-immunogenic compounds comprising either polymers or non-polymers have been used as a platform or carrier molecule to which is conjugated a B-cell epitope derived from an allergen or a known self-antigen. While it is believed the prior art shows that conjugates of nonimmunogenic carrier molecules and haptens or DNA may be used to induce B cell tolerance (anergy/unresponsiveness) in allergies and auto-immune diseases, it is also believed that the prior art fails to disclose, nor is it obvious therefrom, that B cell tolerance may be induced for therapeutic purposes in either cancer or microbial infections. On the contrary, the current belief of those skilled in the art is that the humoral response is important, if not critical, in the development of protective immune response; i.e., an anti-tumor response or an anti-microbial response.

SUMMARY OF THE INVENTION

Accordingly, it is a primary object of the present invention to provide compositions for treating diseases, such as certain cancers and microbial infections, exacerbated by the presentation to antigen-specific B cells of a soluble antigen comprising repeated, antigenic carbohydrate determinants.

It is another object of the present invention to provide a composition comprising a conjugate of a substantially non-immunogenic carrier molecule and a B cell toleragen comprising a suppressive amount of a repeated, antigenic carbohydrate determinant derived from a shed antigen involved in exacerbation or promotion of a disease selected from the group consisting of certain cancers and microbial infections.

It is another object of the present invention to provide a method of making a composition comprising a substantially nonimmunogenic carrier molecule linked to a B cell toleragen comprising a suppressive amount of a repeated, antigenic carbohydrate determinant of a shed antigen involved in exacerbation or promotion of a disease selected from the group consisting of certain cancers and microbial infections.

It is a further object of the present invention to provide methods of treating an individual, having a disease selected from the group consisting of a certain type of cancer or microbial infection, using a therapeutically effective amount of a composition comprising a substantially nonimmunogenic carrier molecule linked to a B cell toleragen comprising a suppressive amount of a repeated, antigenic carbohydrate determinant of a shed antigen involved in exacerbation or promotion of that particular disease.

It is a further object of the present invention to provide a composition and method for anti-tumor therapy which is directed to a subpopulation of B lymphocytes present in an individual. In that regard, such B cells promote tumor progression of the primary tumor, and such B cells may be located in lymphoid tissues containing shed tumor antigen, as well as circulating in body fluids of the individual.

It is an additional object of the present invention to provide a composition and method for anti-parasitic therapy directed to a subpopulation of B lymphocytes present in an individual infected with certain Leishmania species. In that regard, such B cells promote disease exacerbation and severity, and such B cells may be located in lymphoid tissues containing shed leishmanial antigen, as well as circulating in body fluids of the infected individual.

The foregoing objects are achieved by identifying (a) a novel mechanism by which a shed antigen, released from a solid, nonlymphoid tumor, induces (activates) a subpopulation of B cells to differentiate into plasma cells which secrete anti-shed tumor antigen antibody that can form immune complexes which can induce a promotion of tumor progression; and (b) a novel mechanism by which a shed antigen, released from an infecting Leishmania species, induces (activates) a subpopulation of B cells, to proliferate, and differentiate into plasma cells which secrete anti-shed leishmanial antigen antibody that can form immune complexes which can promote exacerbation of the disease process and subsequent dissemination of the parasite throughout the infected individual.

In one embodiment of the present invention, in an individual, B cells are tolerized with a suppressive amount of a repeated, antigenic carbohydrate determinant of the shed tumor antigen, thereby tolerizing shed tumor antigen-specific B cells in a manner that inhibits involvement of such B cells in a pro-tumor immune response. In another embodiment of the present invention, in an individual infected with a leishmanial species capable of causing disseminated disease, B cells are tolerized with a suppressive amount of a repeated, antigenic carbohydrate determinant of the shed leishmanial antigen, thereby tolerizing shed leishmanial antigen-specific B cells in a manner that inhibits the role of such B cells in the disease promotion(e.g., disease exacerbation). In either embodiment, administered to the affected individual is a therapeutically effective amount of a composition comprising a substantially nonimmunogenic carrier molecule and a suppressive amount of a repeated, antigenic carbohydrate determinant of the relevant shed antigen.

An additional mode of therapeutic benefit of the conjugate according to the present invention is that when administered in vivo, the composition will compete with the shed antigen (containing an immunostimulatory number of repeated, antigenic carbohydrate determinants) for anti-shed antigen antibody. The result of such competition will be the reduction of the formation of immune complexes containing shed antigen (i.e. by the formation of immune complexes containing the composition). Since Fc receptors on activated immune effector cells (and tumor cells) may be preferentially crosslinked when immune complexes contain an immunostimulatory number of repeated, antigenic carbohydrate determinants (e.g., containing shed antigen) because of a threshold level for spacing and number required for receptor crosslinking, and the crosslinking of such receptors is a signal that plays an important role in the production of mediators of disease progression, reducing the formation of such immunostimulatory immune complexes containing repeated antigenic determinants may also reduce the respective disease progression.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
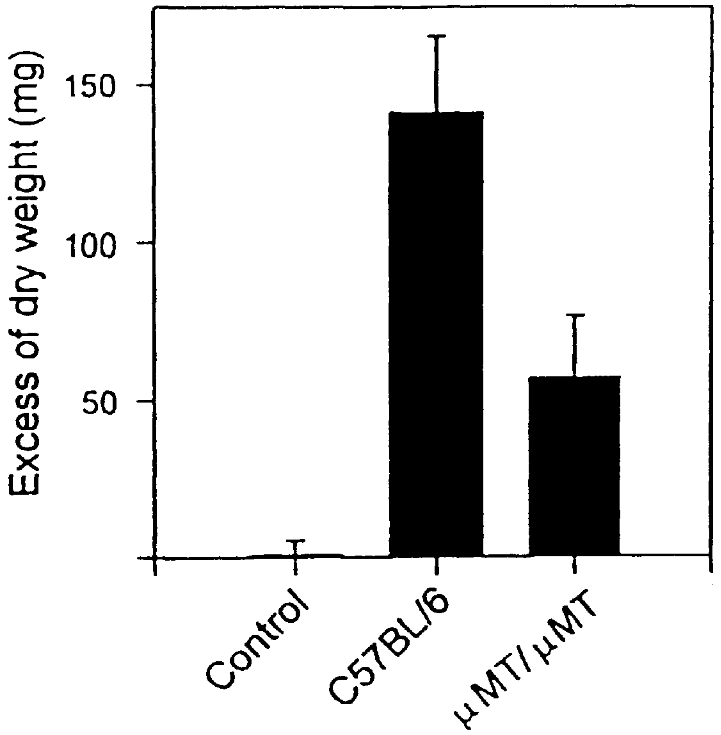
FIG. 1 is a bar graph illustrating a comparison between subcutaneous tumor growth in mice having an absence of functional B cells (C57B/$\mu$TM/$\mu$MT mice) as compared to B cell competent (C57BL/6) mice.

The term "lymphoid tissue" is used herein, for purposes of the specification and claims, to mean a tissue which contains localized areas of antigen presenting cells (e.g., follicular or germinal center dendritic cells) and B lymphocytes, and in which can be induced an immune response involving B cells. An example of such localized areas comprises germinal centers. Such lymphoid tissues comprise lymphatic tissues including, but not limited to, lymph nodes, milky patches in the mesenterium of the intestine, omentum, appendix, Peyer's patches, loose connective tissue (e.g., associated with vessels in the walls of the aorta), lymphatic vessels, submucosal spaces, subserosa spaces, peritoneal cavity, ligaments (e.g., gastrohepatic ligament), artherosclerotic plaques containing trapped B cells, and epineura.

The term "B cells" is used herein in relation to solid non-lymphoid tumors and leishmanial infections, and for purposes of the specification and claims, to mean antigen specific B lymphocytes which have a cell surface receptor that includes, but is not limited to, surface immunoglobulin comprising antibody against a shed antigen, or a select in having binding specificity for shed antigen. Binding of such receptor with shed antigen (by itself or as presented by follicular or germinal center dendritic cells) may activate (by itself or in the presence of another B cell stimulatory factor, such as may be displayed by presenting follicular or germinal center dendritic cells) the B cells to proliferate and/or differentiate into plasma cells capable of secreting anti-shed antigen antibody. Antigen specific B cells comprise B cells activated by shed antigen such as mature B cells and/or memory B cells.

The term "solid, non-lymphoid tumor" is used herein, for purposes of the specification and claims, to mean any primary tumor (a) of ductal epithelial cell origin, including tumors originating in an organ such as liver, lung, brain, bone marrow, adrenal gland, breast, colon, pancreas, stomach, prostate, gastrointestinal tract, or reproductive tract (cervix, ovaries, endometrium etc.), or metastases thereof; and (b) which secretes or produces shed antigen (e.g., serous, or endometroid, or mucinous tumors). For the purposes of the present invention, "solid, non-lymphoid tumor" may also include melanoma.

The term "organ" is used herein, for purposes of the specification and claims, to mean any tissues or organs in which solid, non-lymphoid tumors, or their metastases, may develop. Such organ may include, but is not limited to, liver, lung, brain, lymph node, bone marrow, and adrenal gland.

The term "antigenic" is used herein, for purposes of the specification and claims, to mean that the substance or molecule referred to may be specifically bound by an antibody molecule. A "carbohydrate determinant" refers to that specific portion (comprising a carbohydrate) of the substance or molecule to which the antibody binds.

The term "shed antigen" is used herein, for purposes of the specification and claims, to mean a glyco-molecule (glycoprotein or glycolipid or carbohydrate-containing molecule) which:

(a) by itself, or in an aggregated or oligomeric (e.g., two or more monomers which are associated with each other by a covalent or noncovalent or other force which mediates contact between the monomers) form, has a molecular size equal to, or greater than, about 100 kilodaltons;

(b) is released (e.g., shed) from cells (e.g., tumor cells or microbial cells) thereby becoming soluble and allowing movement to reach B cells (e.g., in lymphoid tissues) which are regional or distal to the site of the cells releasing the shed antigen;

(c) comprises a polyvalent molecule comprised of multiple carbohydrate chains, and a repeated, carbohydrate antigenic determinant comprising a carbohydrate or a combination of carbohydrates (e.g., N-acetyl galactosamine (GalNAc) such as Tn antigen, or other GalNAc-containing epitopes; an epitope comprising a sialic acid (NeuAC) such as sTn antigen, or a sialic acid-containing epitope other than sTn antigen; a combination of a GalNAC and NeuAc; mannose (Man); galactose (Gal); arabinose; a combination of Gal and Man; or other combinations thereof);

(d) is capable of inducing a humoral immune response resulting in the production and secretion of anti-shed antigen antibody which may be predominately of an IgG class (suggestive of, at least in part, a T independent antibody response); and (e) can interact with anti-shed antigen antibody in forming immune complexes, wherein the immune complexes may bind and cross-link Fc receptors (e.g., FcγRI) present on the surface of Fc receptor-expressing cells.

Additionally, and relevant to shed antigen comprising shed tumor antigen, shed tumor antigen can be produced by cells with altered glycosylation (e.g., underglycosylated, incompletely glycosylated, partially deglycosylated, or in an altered conformational) form as compared to the glycosylation pattern of the same molecule typically found exposed on most normal cells (e.g., nonmalignant cells or non-precancerous cells, or cells not involved in the neoplastic disease process).

With regard to the antigen being shed, specifically the antigen is noncellular. For example, non-cellular tumor antigen consists essentially of soluble tumor antigen that is not an integral part of a living tumor cell. Such shed tumor antigen exists in a form selected from the group consisting of free form (shed tumor antigen alone), in an immune complex form (shed tumor antigen bound to anti-shed tumor antigen antibody), in a form as presented on the surface of a follicular or germinal center dendritic cells (antigen presenting cell), in a form as bound to the cell surface of B cells, and as a form in tumor cell membranes existing apart from living tumor cells (e.g., soluble membrane complexes representing portions of dead tumor cells). Similarly, non-cellular leishmanial antigen consists essentially of soluble leishmanial antigen that is not an integral part of a living promastigote or amastigote. Such shed leishmanial antigen exists in a form selected from the group consisting of free form (shed leishmanial antigen alone), in an immune complex form (shed leishmanial antigen bound to anti-shed leishmanial antigen antibody), in a form as presented on the surface of a follicular or germinal center dendritic cells (antigen presenting cell), in a form as bound to the cell surface of B cells, and as a form in the protozoan membranes existing apart from living organisms (e.g., soluble membrane complexes representing portions of dead promastigotes or amastigotes).

With regard to the shed antigen being a glycomolecule in composition, having repeated, antigenic carbohydrate determinants, and being about 100,000 daltons or larger in molecular size, these features appear to be essential for the shed antigen to provoke an immune response that is disease promoting or exacerbating in an individual. Without intending to be bound by theory, the size of the shed antigen (including the number of repeats), and the spacing between its repeated antigenic carbohydrate determinants influence antigen presentation, and enable the induction of a B cell immune response without requiring the assistance of T cells. Additionally, the size of the shed antigen (including the number of repeats), and the spacing between its repeated antigenic carbohydrate determinants, and antibody bound to the repeated antigenic carbohydrate determinants, influence the formation of immune complexes, and the presentation of the immune complexes to immune effector cells (and/or tumor cells, in the case of a solid, nonlymohoid tumor) which may then mediate disease progression. Further, it is believed that the shed antigens, containing a threshold number (immunostimulatory) of repeated antigenic carbohydrate determinants, may cause a chronic stimulation of B cells which may interfere with the normal maturation of a humoral response effective for resisting disease, and thereby favor disease progression.

For purposes of illustration, and not limitation, and with regard to solid, nonlymphoid tumors, exemplifying such shed antigens from tumor are mucins and mucin-like molecules. Briefly, mucins are high molecular weight glycoproteins (e.g., greater than about 100 kiloDaltons (kD) in molecular mass) of which a significant portion of the polypeptide backbone comprises a domain composed of a tandomly repeating peptide subunits (e.g. about 20 to about 125 repeats). Typically in mucin and mucin-like molecules, each tandemly repeated peptide is capable of being glycosylated; and hence, mucin and mucin-like molecules contain multiple carbohydrate chains. The repeated, antigenic carbohydrate determinant comprises an epitope occurring in the carbohydrate chains of mucin and mucin-like molecules. In processes such as transformation or tumor development, and due to various factors (e.g., the increased production of mucin, lack of availability of glycosyltransferases), tumor cells produce mucin or mucin-like molecules with altered glycosylation. An immune response against mucin or mucin-like molecules produced by tumor cells is thought to be primarily directed against one or more carbohydrate epitopes as a result of the altered glycosylation. For example, because of the altered glycosylation, shed tumor mucin has one or more epitopes not normally found on mucin or has one or more epitopes which may be found on mucin but which is not normally exposed to the immune system. Such epitopes may include repeated antigenic carbohydrate determinants comprising the sialyl Tn (sTn) antigen (comprising the NeuAc portion of NeuAcα2→6GalNAcα1→O-Ser- or Thr); or the Tn antigen (comprising the GalNAc portion of GalNAcα1→O-Ser- or Thr); or other sialic acid containing epitopes (e.g., comprising NeuAc α2 on the carbohydrate chains (a) NeuAcα2→6Gal→O-Ser-or Thr, (b) NeuAcα2→3Gal→-O-Ser-, or (c) NeuAcα2→3GalNAc→-O-Ser- or Thr); or a combination thereof (e.g., comprising both the sTn antigen and Tn antigen). An example of a mucin-like glycoprotein which is produced by tumor cells in a form with altered glycosylation, and is shed by tumor cells, is SSEA-1 antigen. An example of a mucin which is produced by tumor cells in a form with altered glycosylation, and is shed by tumor cells, is mucin-1 (MUC1, or polymorphic epithelial mucin). Other exemplary molecules shed from tumor cells include those listed in Table 1.

TABLE 1

| Soluble-tumor Ag | Antibody | Characteristic |
|---|---|---|
| sialyl SSEA-1 ("SLX")[1] | FH-6 | pancreatic, lung, gastric, ovarian, cervical adeno-carcinomas |
| PA8-15[2] | mAb PA8-15 | pancreatic, gastro-intestinal carcinoma |
| MUSE 11[3] | mAb MUSE 11 | adenocarcinoma, pancreatic cancer |
| Her-2/neu[4] | mAb GFD-OA-p185-1 | 185 kD; various carcinomas |
| TA90[5] or U-TAA[5] | mAb ADI-40F4 | melanoma |
| KL-6 antigen[6] | mAb Kl-6 | various adenocarcinomas |

[1]Lee et al., 1992 J. Formos. Med. Assoc. 91:760–3.
[2]Arai et al., 1990, Jpn. J. Clin. Oncol. 20:145–53.
[3]Takai et al., 1991, Nippon Shokakibyo Gakkai Zasshi, 88:170–4.
[4]Meden and Kuhn, 1997, Eur. J. Obstet. Gynecol. Reprod. Biol. 71:173–9.
[5]Hsueh et al., 1998, J. Clin. Oncol. 16:2913–2920; Euhus et al., 1990, Int. J. Cancer 45:1065–70.
[6]Kohno et al., 1989, Cancer Res. 49:3412–9.

For purposes of illustration, and not limitation, in a preferred embodiment of the present invention, the shed antigen comprises shed tumor antigen comprising the gene product of the MUC-1 gene (the product known as mucin-1 or polymorphic epithelial mucin) having repeated, antigenic carbohydrate determinants. Mucin-1 is a pan-carcinoma antigen present in a majority of mucinous carcinomas. In this preferred embodiment, the repeated, antigenic carbohydrate determinant is comprised of one or more epitopes selected from the group consisting of the sialosyl Tn ("sTn"), Tn, or a combination thereof (e.g., comprising both the sTn antigen and Tn antigen). It is believed that mucin-1, produced by tumor cells, displays carbohydrate chains comprising NeuAcα→6GalNAcα1→O-Ser- or Thr-(polypeptide backbone) or shorter, differentially glycosylated chains. In contrast to whole tumor cells expressing mucin, shed tumor mucin can induce an antibody response and T helper cell response ($TH_2$), but not cytotoxic T cell responses (Apostolopoulos et al., 1994, *Cancer Res.* 54:5186). How-ever, it was not known that an immune response against shed tumor mucin may promote tumor cell growth and metastasis. This is an unexpected result as it has been reported that only mucin isoforms lacking repeated antigenic determinants can potentiate tumor (Baruch et al., 1997, *Int. J. Cancer* 71:741–9). Further, current clinical trials involve injection of repeated antigenic determinants of mucin with the objective, and result, of inducing more anti-mucin antibody (see, e.g., Miles et al., 1996, *Br. J. Cancer* 74:1292–6; Finn et al., 1995, *Immunol. Rev. No.* 145:61–89).

For purposes of illustration, and not limitation; and with regard to Leishmania, exemplifying such shed antigens from leishmanial species may include stage specific and/or constitutively expressed carbohydrate-containing antigens that are released from the protozoan. Some of these shed antigens appear to be conserved in a majority of leishmanial species analyzed. However, the number of repeated, antigenic carbohydrate determinants in the shed antigen may vary amongst different leishmanial species. Accordingly, it is possible that those leishmanial species that tend to cause a disseminating, highly destructive disease may differ in the number of repeated, antigenic carbohydrate determinants in the shed antigen as compared to that of less virulent leishmanial species. A general hypothesis has been made that Leishmania species may express disease promoting epitopes which are different from epitopes mediating resistance, thereby raising the question of what comprises such epitopes (Bogdan et al., 1990, *Eur. J. Immunol.* 20:2533–40). In a preferred embodiment of the invention, the shed antigen of Leishmania is lipophosphoglycan ("LPG") comprised of a lipid portion and phosphoglycan repeat structure (phosphorylated oligosaccharide repeat branches). LPG can be found anchored to the surface of the leishmanial parasite, and is shed from the parasite. This glycolipid, by itself (as opposed to when complexed with protein), appears ineffective at stimulating T cell proliferative responses (Russo et al., 1992, *J. Immunol.* 148:202–7). Anti-LPG antibodies may be substantially directed against an epitope comprising one or more of a combination of galactose and mannose (e.g., Galβ1-4Man), and the highly immunogenic P3 epitope ($PO_4$-6[Galβ1-3]Galβ1-4Manaα1-. With regard to an immune response to leishmanial antigen, it is known that whether a Th1 response or a Th2 response is induced depends on the type of leishmanial antigen, and the mode in which the antigen is administered (Liew et al., 1990, supra). However, it was not known that a humoral immune response may promote/ exacerbate the progressive disease caused by the infecting leishmanial species by formation of immune complexes which may interact with activated immune effector cells in inducing a disease exacerbating response including an inflammatory response which promotes invasion and dissemination by the parasite.

The term "individual", when used herein specifically in relation to solid, nonlymphoid tumor, for purposes of the specification and claims, means a mammal, and preferably a human, that comprises an individual having a primary tumor comprising a solid, non-lymphoid tumor and/or its metastases; or an individual with a pre-cancerous condition comprising transformed (abnormal in proliferation and/or genetic makeup as compared to normal epithelial cells of the same type) cells of ductal epithelial origin which release shed tumor antigen; or an individual who is at high risk for developing a solid, non-lymphoid tumor; or an individual who has been treated for a solid, nonlymphoid tumor and thereby inherently carries a risk of recurrence.

The term "disease progression" is used herein, for purposes of the specification and claims, to mean one or more of tumor progression and progression of disease caused by leishmanial infection. Tumor progression may one or more of promoting tumor growth, promoting metastasis, or advancing the stage of malignancy. Where disease progression involves Leishmania, disease progression may include, but is not limited to, enhancement of leishmanial parasite dissemination(invasion) and resultant disseminated disease.

The term "immune effector cells" is used herein, for purposes of the specification and claims, to mean granulocytes (primarily neutrophils, but may include eosinophils) and macrophages which: express or are activated to express functionally significant and detectable FcγRI; and are induced by immune complex crosslinking to release one or more of enzymes, cytokines, oxygen free radicals, and angiogenic factors which promote disease progression.

The term "tolerance" is used herein, for purposes of the specification and claims, to mean an immunologic tolerance of B cells specific for shed antigen. Tolerance is an induced unresponsiveness to shed antigen as the result of antigen-induced functional inactivation or death of B cells specific for that antigen, while not effectively stimulating an antibody response against shed antigen. For example, after administering a composition according to the present invention, the composition, via its suppressive amount of a repeated, antigenic carbohydrate determinant, contacts B cells which display a surface immunoglobuin specific for the epitopes. Such contact may induce tolerance of the contacted B cells characterized by a property which may include, but is not limited to, one or more of: a cross-linking of B cell surface immunoglobulins thereby inducing apoptotic death; inducing clonal deletion; inducing apoptosis; blocking interaction with shed antigen; blocking of B cell function; functional inactivation of B cells; cytolysis of B cells; causing a B cell dysfunction which results in a therapeutic benefit; reduction in the number of B cells; and inhibiting the proliferation of B cells and/or inhibiting the differentiation of B cells to plasma cells, upon subsequent interactions with that determinant. The term "tolerance" may also be used herein, for purposes of the specification and claims, to mean an immunologic tolerance caused by the reduction in immune complexes containing shed antigen. Reduction of such immunostimulatory immune complexes may reduce interaction with immune effector cells that are activated by such immune complexes to produce mediators of inflammation involved in disease progression. Also, some antigen presenting cells (e.g., dendritic cells) may retain such immune complexes on their surface, and present the shed antigen portion of the immune complex to B cells in inducing the B cells to produce more plasma cells which secrete more anti-shed antigen antibody. Thus, reduction of such immunostimulatory immune complexes may reduce shed antigen presentation to B cells.

The term "substantially non-immunogenic" is used herein in relation to a composition according to the present invention, for purposes of the specification and claims, to mean that the composition, when it is administered to an individual, is weakly effective or ineffective in inducing an antibody producing response, and may also be weakly effective or relatively ineffective in stimulating T cells, as compared to the respective activity of the shed antigen appearing in its immunostimulatory form.

The term "immune effector cells" is used herein, for purposes of the specification and claims, to mean one or more cell populations present in the affected individual, wherein the cell populations may include, but are not limited to, antigen presenting cells (e.g., follicular dendritic cells), macrophages, granulocytes, and endothelial cells. Many types of immune effector cells play a role in an inflammatory response, whether as in antigen presenting role, or in a role in which enzymes (e.g., tissue degrading enzymes), cytokines, or angiogenic factors are released which assist in mediating inflammation (and also in promoting disease progression).

The term "immunostimulatory" is used herein in relation to shed antigen, and for purposes of the specification and claims, to mean that the number of repeated, antigenic carbohydrate determinants, and the spacing between the repeated, antigenic carbohydrate determinants, reach a threshold that influences antigen presentation to B cells in stimulating a humoral immune response against the repeated, carbohydrate antigenic determinants. For purposes of illustration, but not limitation, the average number of repeats of P3 unit per immunostimulatory molecule of leish-manial LPG is approximately 30–36. The term "immunostimulatory" is also used herein, in relation to immune complexes formed between shed antigen and anti-shed antigen antibody, and for purposes of the specification and claims, to mean that such immune complexes are capable of interacting with immune effector cells in initiating a cascade of inflammatory processes that mediate disease progression. For example, the spacing and number of antibodies in such immune complexes reach a threshold that influences binding to (e.g., favors binding to and crosslinking of) Fc receptors on immune effector cells and/or tumor (i.e., when it is shed tumor antigen) resulting in an inflammatory process that may contribute to disease promotion.

The term "carbohydrate chain" is used herein in relation to a repeated, antigenic carbohydrate determinant, and for purposes of the specification and claims, to mean a molecule that comprises one or more repeated, antigenic carbohydrate determinants. The carbohydrate chain may further comprise a moiety (e.g., chemical group, linker, molecule, amino acid) that may be used to link the carbohydrate chain to a substantially non-immunogenic carrier molecule in forming the tolerogenic composition according to the present invention, as will be more apparent from the following descriptions. For example, where the moiety is an amino acid, the carbohydrate chain comprises a glycopeptide.

The term "suppressive amount" is used herein in relation to a repeated, antigenic carbohydrate determinant or a carbohydrate chain comprising a repeated, antigenic carbohydrate determinant, and for purposes of the specification and claims, to mean that a sub-immunogenic number, spacing, and density of repeated, antigenic carbohydrate determinants that are linked to a substantially non-immunogenic carrier molecule in forming the tolerogenic composition according to the present invention. This means that the amount of the determinants in the composition are below (or less than) the threshold needed for antigen presentation that induces an antibody producing response (see, for example, U.S. Pat. Nos. 5,126,131, 5,268,454, and 5,276,013); and the density of the determinant of the determinants is sufficiently high enough to induce tolerance of B cells. Thus, the composition is tolerogenic, and relatively ineffective in inducing a humoral immune response. It will be appreciated by those skilled in the art, the density of the repeated, antigenic carbohydrate determinant on the substantially non-immunogenic carrier molecule will depend on such factors as the molecular mass of the substantially non-immunogenic carrier molecule, and the molecular mass of the repeated, antigenic carbohydrate determinant. Since in a preferred embodiment the molecular mass of the composition is less than 100,000 daltons, the density of the repeated, antigenic carbohydrate determinant is the maximum number, or a number approaching the maximum number, of the determinants that can be linked to the carrier molecule while still maintaining a size of the resultant tolerogenic composition as less than 100,000 daltons. In a more preferred embodiment, with consideration of maintaining a size of the composition as being less than 100,000 daltons, the density of the repeated, antigenic carbohydrate determinant is a number in the range of from about 6 to about 20; where greater than 20 would also be preferable as long as the size of the resultant composition is less than 100,000 daltons. For purposes of illustration, but not limitation, the spacing between molecules of the repeated, antigenic carbohydrate determinant, on the substantially non-immunogenic carrier molecule, may be between about 100 Ångstroms to about 200 Ångstroms.

Additionally, when the composition becomes part of an immune complex, such immune complexes may be less efficient in binding Fc receptors than immune complexes containing immunostimulatory shed antigen.

The terms "pro-tumor immune response" and "immune complex mediated tumor progression" are used interchangeably herein, for purposes of the specification and claims to mean a humoral immune response against a repeated, antigenic carbohydrate determinant of shed tumor antigen that results in immune complexes formed between antibody (particularly IgG1) to shed tumor antigen and shed tumor antigen. Such immune complexes may then promote tumor progression by one or more mechanisms including, but not limited to: binding and crosslinking FcγRI on immune effector cells resulting in the release of inflammatory mediators which promote angio-genesis for, and invasion by, tumor cells; binding and crosslinking FcγRI on FcγRI-expressing tumor cells resulting in an induction of tumor cell proliferation, and an increase in the amount of shed tumor antigen released by the tumor cells; and binding and crosslinking FcγRI on FcγRI-expressing endothelial cells resulting in an induction of endothelial cell proliferation and/or release of factors promoting angiogenesis.

The present invention relates to the discovery of a novel mechanism in which shed antigen can activate B cells present in lymphoid tissues (located proximal or distal to a primary site from which the shed antigen migrates) which can result in the production of plasma cells; the plasma cells produced can secrete anti-shed antigen antibody; the anti-shed antigen antibody can complex with shed antigen in forming immune complexes, and such immune complexes can interact with immune effector cells and/or other FcγR1-expressing cells in stimulating processes that may promote disease progression. In a preferred embodiment, anti-shed tumor antigen antibody of an IgG isotype is capable of complexing with shed tumor antigen in forming immunostimulatory immune complexes. The immunostimulatory immune complexes contact and interact with host cells (e.g., one or more of immune effector cells, FcγR1-expressing tumor cells, and FcγR1-expressing endothelial cells) in inducing the immune effector cells to respond in a manner that can promote tumor progression. This mechanism involves the specific type of immune response induced by shed antigen. This specific immune response, a pro-tumor immune response, involves (a) the contact or presence of shed antigen, in relation to the cell surface of B cells; (b) activation of such B cells to proliferate and/or differentiate into plasma cells; and (c) production by the plasma cells of anti-shed antigen antibody in sufficient amounts which may act indirectly and/or directly to mediate disease progression, by mechanisms as previously described herein in more detail.

EXAMPLE 1

In this example, illustrated is (a) B cell involvement, and the pro-tumor immune response related thereto, capable of promoting tumor progression; and (b) the effect of an immunological response involving shed antigen-specific B cells in promoting disease progression. While the disease progression illustrated in this example is tumor (solid, nonlymphoid tumor) progression, it will be apparent to one skilled in the art from the following description that a similar immunological response can occur in disease progression other than tumor progression. Relevant to some of the following illustrations, it is important to consider the following concept. Various strains of mice were used as a standard animal model for evaluating whether a B cell response may be involved in tumor progression, including promoting metastasis. In tumor bearing mice of B cell competent strains, a similar proliferative germinal center B cell response was observed in lymph nodes regional to a primary tumor as observed in tumor bearing humans. Further, mice having immune deficiencies have been accepted as a standard in vivo model for assessing therapeutic approaches to human B cell proliferation (see, e.g., Durandy et al., 1992, J. Clin. Invest. 945–952). Additionally, we have demonstrated that the B cell population in patients having tumor progression and a pro-tumor immune response can contain a subpopulation of shed tumor antigen-specific B cells.

1.1 A Lack of B Cells Correlates with a Decreased Ability to Mediate Tumor Progression in vivo To assess whether B cells are effector cells of, at least in part, a pro-tumor immune response, an in vivo standard experimental model was used. One group of C57 $\mu$MT/$\mu$MT ("B cell deficient"; i.e., do not develop competent B cell system) mice was injected intrasplenically with $10^6$ B16F10 melanoma tumor cells. One group of C57BL/6 (immunocompetent) mice was injected intrasplenically with $10^6$ B16F10 tumor cells. One group of mice (control) received PBS only. Fourteen days postinjection, spleens from the three groups of mice were evaluated for tumor growth (progression) by measuring spleen weight. For spleen weight determinations, the spleens were removed; dried by immersion in 100% ethanol for seven days during which period the ethanol evaporated; and the dried spleens were weighed, and an average for the group reported. As shown in FIG. 1, the spleen weight was significantly decreased in B cell deficient (C57 $\mu$MT/$\mu$MT) mice, as compared to B cell-competent mice, indicative of a decreased ability of B cell deficient mice to mediate tumor progression.

Figure 2:
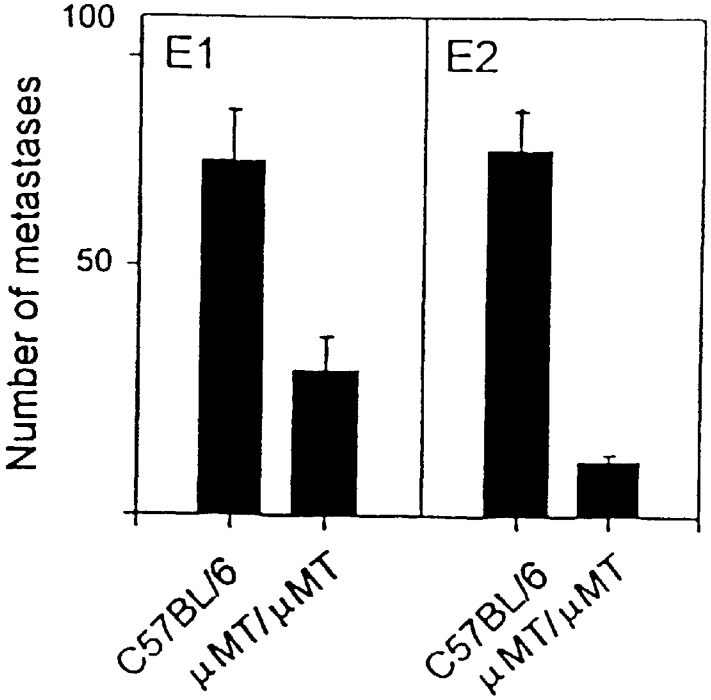
FIG. 2 is a bar graph illustrating the average number of lung metastases in B cell deficient (C57B/$\mu$MT/$\mu$MT) mice as compared to B cell competent (C57BL/6) mice.

Lung metastases formation involves cell arrest (non-anchorage conditions), extravasation (anchorage condition) and colony formation (anchorage/non-anchorage conditions). To assess whether B cells are effector cells (at least in part) of a metastatic effect, a model for metastatic growth was used. It is known by those skilled in the art that injection of B16F10 cells via the tail vein of mice typically results in the formation of lung metastases. One group of C57BL/6 mice was injected via the tail vein with $10^6$ B16F10 cells. One group of C57 $\mu$MT/$\mu$MT mice was injected via the tail vein with $10^6$ B16F10 cells. Fourteen days postinjection, the lungs from the two groups of mice were evaluated for tumor growth macroscopically, and the number of metastases counted. As shown in FIG. 2 (E1 and E2 are duplicate experiments), the average number of lung metastases was significantly decreased in B cell deficient (C57 $\mu$MT/$\mu$MT) mice as compared to immunocompetent (C57BL/6) mice. The significant decrease also represents the lack of several of the B cell deficient mice to develop any detectable metastases in the lung.

In summary, the results illustrated in FIGS. 1 and 2 indicate that there is a decreased ability of B cell deficient mice to mediate tumor progression (including metastasis) as compared to normal mice; thus, providing evidence of a subpopulation of B cells in a pro-tumor immune response which can mediate tumor progression.

Figure 3:
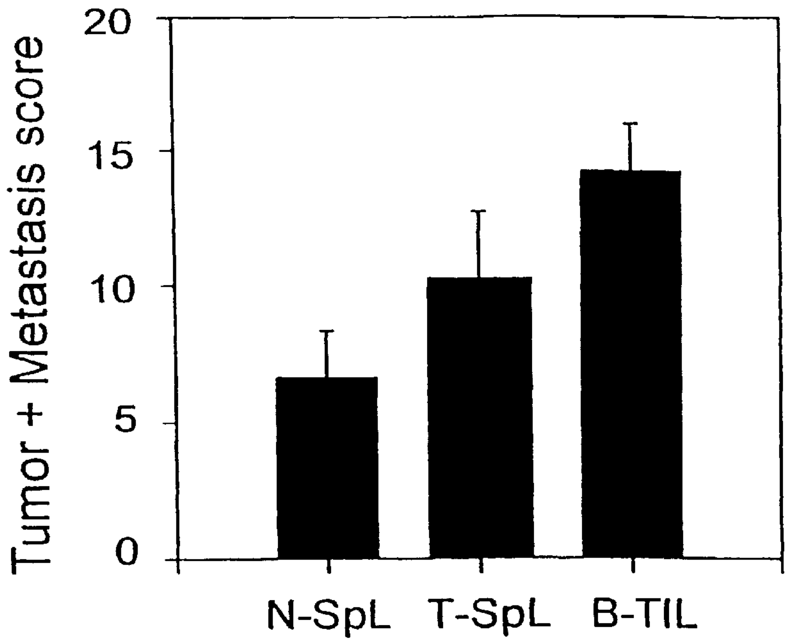
FIG. 3 is a bar graph illustrating in vivo spleen tumor cell growth and liver metastasis (combined score) in the presence of splenic B lymphocytes from tumor bearing mice (T-SpL), B lymphocytes from tumor (B-TIL), and splenic B lymphocytes from normal mice (N-Spl).

1.2 B Cells Involved in Tumor Promotion include those Exposed to Shed Tumor Antigen To assess whether different populations of B lymphocytes could promote growth of the tumors in vivo, tumor growth in CH3 mammary gland tumor bearing mice was compared when the mice were injected every 2 days for a 14 day period with either B lymphocytes (50,000 cells) isolated from normal mouse spleen; B lymphocytes isolated from lymphoid tissues (e.g., spleens) of tumor bearing mice (50,000 cells), or tumor infiltrating B lymphocytes (B-TIL; 50,000 cells) isolated from tumors of tumor bearing mice. Isolations of B lymphocytes were performed by magnetic separation methods known in the art. After the 14 day period, liver metastasis and spleen tumor growth (tumor+metastasis score) were evaluated and scored. As shown in FIG. 3, B-TIL and B lymphocytes from spleens of tumor bearing mice ("T-Spl") each promoted statistically significant tumor growth and metastasis in vivo, whereas B lymphocytes from normal spleen ("N-Spl") did not enhance either tumor growth or metastasis. An important conclusion that can be drawn from these results is that to gain the ability to promote tumor growth, B lymphocytes must first be exposed to tumor antigens (e.g., prior contact with shed tumor antigen); i.e., shed tumor antigen-specific B cells are involved in a pro-tumor immune response.

1.3 Depleting B Cells (including Shed Antigen-Specific B Cells) can interrupt B Cell involvement in a Pro-tumor response in vivo, thereby affecting Tumor Progression Fifty three C3H mice were injected intrasplenically with $10^6$ Met 129 tumor cells (high mucin-producing mammary carcinoma cells). The injected mice were then divided into two treatment groups. One group of 28 mice was injected with an irrelevant (not directed against any specific mouse antigen) goat IgG antibody (170 $\mu$g per injection) at days 5, 7, and 9 following tumor challenge. A second group consisted of 25 mice injected with goat anti-mouse IgG (170 $\mu$g per injection) at days 5, 7, and 9 following tumor challenge. The goat anti-mouse IgG was used to deplete the C3H mice of their B cells, thereby interrupting the host B cell-mediated pro-tumor immune response. At 22 days following tumor challenge, the two groups of mice were analyzed for primary tumor growth in the spleen, metastasis to the liver, and extra-regional metastasis (abdominal lymph nodes). Table 2 shows one experiment in which compared was primary tumor growth, and the incidence of liver metastasis ("Liver Met.") and extra-regional metastasis ("Extra-R Met.") in the mice treated with irrelevant goat IgG ("Goat-IgG"), and mice treated with goat anti-mouse IgG ("Anti-IgG"). Table 2 shows that there is a statistically significant reduction in the incidence of metastasis in the B cell-depleted mice ("Anti-IgG") as compared to the control group receiving irrelevant IgG.

TABLE 2

| Observed | Goat-IgG Control | Anti-IgG |
|---|---|---|
| Tumor | 8 of 8 | 6 of 6 |
| Liver Met. | 5 of 8 | 0 of 6 |
| Extra-R Met. | 6 of 8 | 0 of 6 |

Figure 4:
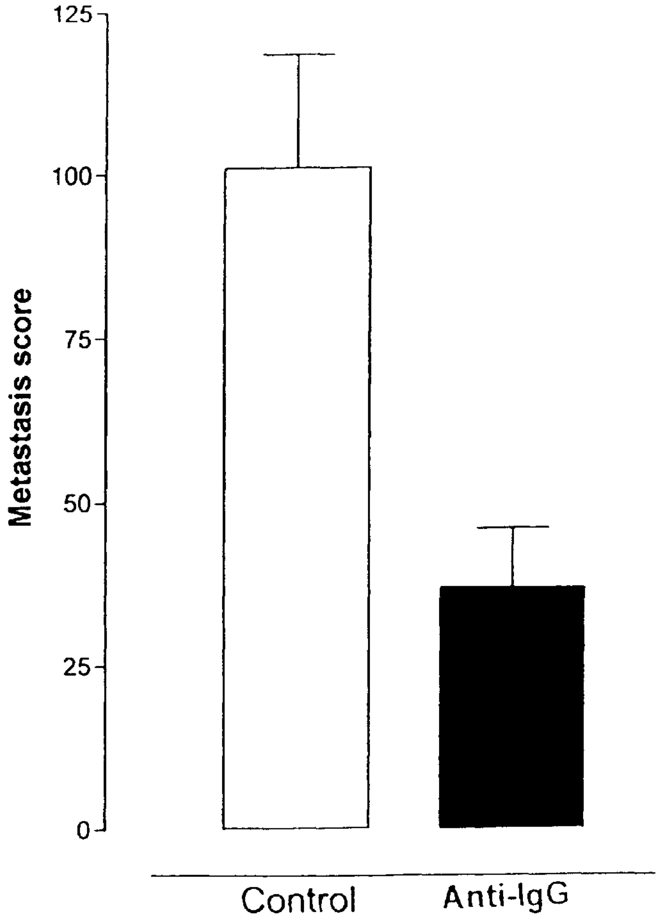
FIG. 4 is a bar graph illustrating the extra-regional (lymph node) and liver metastases scores (combined as "metastasis score") in mice treated with either irrelevant goat IgG, or goat anti-mouse IgG.

As shown in FIG. 4, mice in which B cells were depleted ("Anti-IgG") showed a statistically significant reduction in the incidence of extra-regional metastasis and liver metastasis as compared to the extra-regional metastasis and liver metastasis exhibited by the control group of mice treated with irrelevant goat IgG. The results in FIG. 4 are normalized values from two experiments. It is important to note that at least 50% of the B cell-depleted mice did not develop detectable metastases. In summary, the results illustrated in Table 2, and FIG. 4 further support the finding that depleting functional B cells, such as by inducing tolerance in shed-antigen specific B cells, can inhibit tumor invasion and metastasis. For example, since plasma cells are reported to have a relatively short life span (e.g., several days to a few weeks), by interfering with shed tumor antigen-specific B cells from differentiating into plasma cells, the number of shed tumor antigen antibody-secreting plasma cells may eventually be reduced. A resultant decrease in the amount of such antibody can result in a decrease in the amount of IC, with a resultant decrease in immune complex-mediated tumor progression.

1.4 Anti-Shed Antigen Antibody is involved in promoting Tumor Progression

Figure 5:
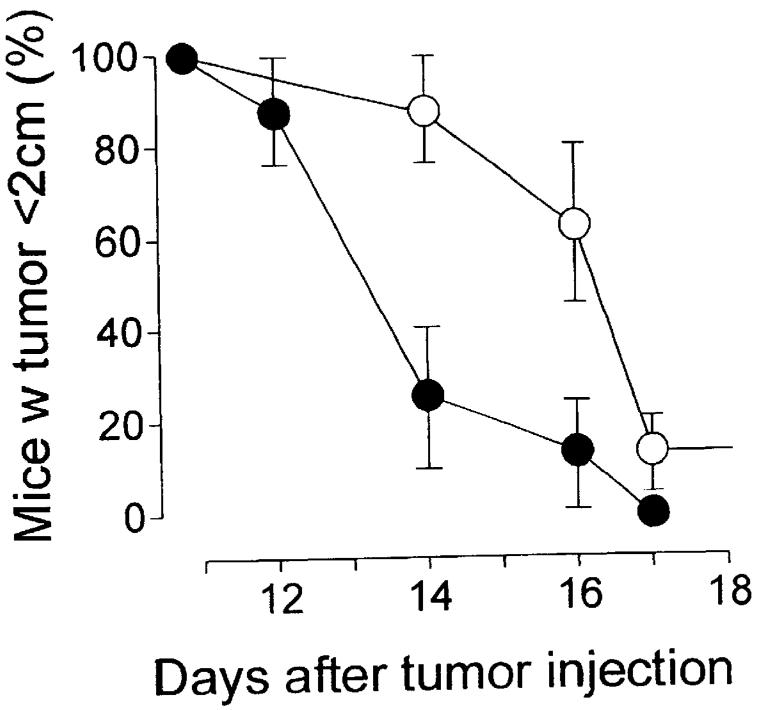
FIG. 5 is a graph illustrating tumor growth in mice having a high anti-sTn antibody titer as compared to mice having a low anti-sTn antibody titer.

To mimic the massive shedding of soluble tumor mucin (with a repeated, antigenic carbohydrate determinant comprising the sTn antigen) that occurs in vivo, injected intravenously into normal C3H mice was a large dose of sTn antigen rich soluble bovine submaxillary mucin ("BSM"; 1 mg in 100 $\mu$l) weekly for a period of three weeks. A control group received injections of saline. Mice receiving BSM showed a significant increase in anti-sTn antibody titer as measured by ELISA. Both the BSM-immunized group and the control group were then injected with $10^6$ living Met 129 carcinoma cells into the mammary pad. Three weeks after tumor cell injection, both groups showed an increased serum anti-sTn antibody titer; however, the BSM-immunized mice showed a titer almost 5 fold higher than the control group. In both groups, tumor growth was measured daily with a caliper. FIG. 5 shows that mice having a high anti-sTn antibody titer (●) developed tumor at a much faster rate than mice having a low anti-sTn antibody titer (○) (statistical significance; $p<0.03$). Hence, the presence of a high titer of antibody against sTn, such as can be induced by shed tumor mucin, promotes tumor growth.

Figure 6:
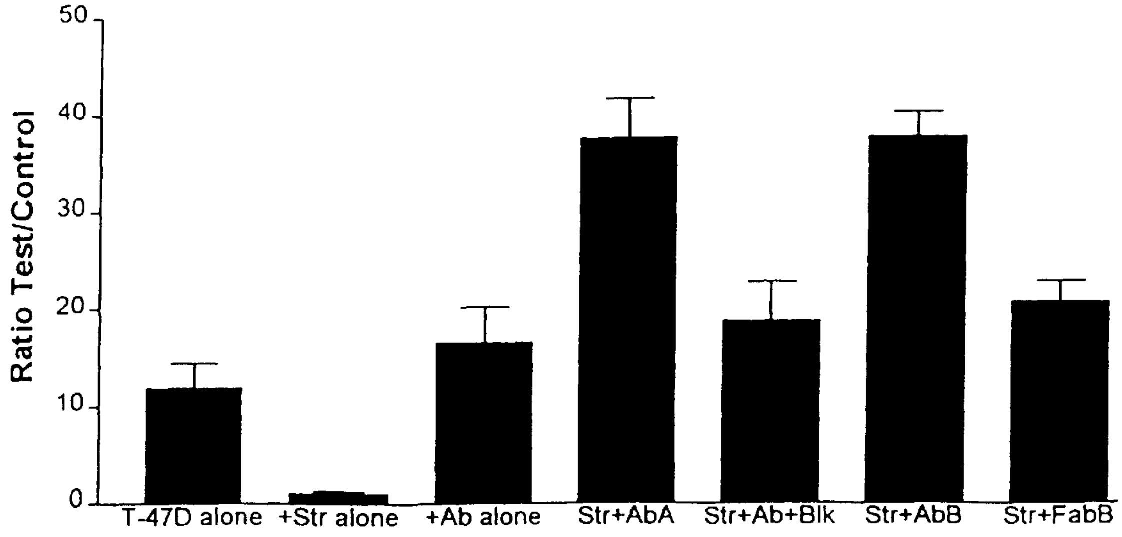
FIG. 6 is a bar graph illustrating invasion of shed tumor antigen-secreting tumor cells through matrix when incubated with various cellular components, antibodies, or antibody fragments.

1.5 A Mechanism by which Anti-Shed Antigen Antibody promotes Tumor Progression This example illustrates only one of several mechanisms which we discovered by which immune complexes comprising anti-shed tumor antigen antibody and shed tumor antigen promote tumor progression. The illustrated mechanism involves the binding by these immune complexes to FcγRI on FcγRI-expressing immune effector cells (one or more of activated neutrophils, activated macrophages, and endothelial cells) with resultant cross-linking of the bound receptors. In one illustration of this mechanism, an in vitro tumor cell invasion assay was used which utilized mucin-secreting human tumor cell line T-47D, a Boyden chamber, and a commercially available basement membrane matrix preparation ("matrix"). In this assay, tested was the ability of tumor cells (2×104 cells) to migrate through the matrix in the following conditions: matrix alone; matrix containing stromal cells (random mixture of granulocytes, monocytes, macrophages, endothelial cells, and fibroblasts; $2\times10_5$ cells); matrix in the presence of anti-sTn mAb (IgG1; 0.06 $\mu$g); matrix containing stromal cells in the presence of anti-sTn mAb; and matrix containing stromal cells in the presence of Fab fragments of the anti-sTn mAb. The plates were incubated at 37° C. in 5% $CO_2$, and fresh media (with or without antibody/antibody fragment, depending on the condition) was substituted every 24 hours. Invasion was measured by counting the number of tumor cells per well which migrated to the bottom of the chamber after 48 to 72 hours. FIG. 6 shows that the maximum invasion through the matrix was observed when the shed tumor antigen-secreting tumor cells were incubated in the presence of stromal cells and either of two anti-sTn mAb tested ("Str +AbA"; and "Str+AbB") as compared to tumor cells alone ("T-47D alone"), or stromal cells ("+Str alone"), or anti-sTn mAb ("+Ab alone), or stromal cells in the presence of Fab fragments of the anti-sTn mAb (Str+FabB). These experiments are further evidence that shed tumor antigen secreted by tumor cells can interact with anti-shed tumor antigen antibody (e.g., of IgG1 subtype) in forming complexes that can activate cells, such as granulocytes and macrophages, to secrete enzymes and/or factors (e.g., one or more of tissue degrading enzymes, cytokines, oxygen free radicals) that promote tumor progression. The involvement of immune complexes, as opposed to the action of antibody alone, was confirmed by using a tumor cell which did not produce sTn-containing shed tumor antigen; i.e., when such tumor cells were incubated in the presence of stromal cells and anti-sTn mAb, there was no increase in tumor invasion as compared to the control values. Additionally, the evidence suggests that immunostimulatory immune complexes comprising anti-shed antigen antibody complexed to shed antigen can have a threshold level for spacing and number of antibody molecules necessary for receptor (FcγRI) crosslinking on immune effector cells and other receptor-bearing cells.

In another illustration of this mechanism, utilized was an in vivo model of tumor progression using SCID mice. One group of SCID mice was injected (subcutaneously) with mucin-secreting human tumor cell line SW620 ($10^5$ cells) alone; one group was injected with SW620 mixed with hybridoma cells ($5\times10^4$) secreting an IgG1 anti-sTn mAb, and a third group (control) was injected with SW620 mixed with hybridoma cells ($5\times10^4$) secreting a control IgG1 mAb (recognizes rabbit LDL receptor). Tumor growth, tumor pathology, angiogenesis (measured as vs$10^{-1}$ mm$^2$), presence or absence of metastasis, and production of shed tumor antigen (e.g., mucin; Table 3, "sTn-mucin") were monitored or measured over an extended period. As shown in Table 3, 20% of the mice injected with SW620 cells alone failed to develop primary tumor during the observed period. Of the 80% that did develop tumor, all failed to develop detectable metastasis. The tumors were characterized as fairly self limiting, necrotic, and with poor angiogenesis. In mice injected with SW620 cells and hybridoma cells secreting an isotype control mAb, 60% failed to develop primary tumor during the observed period. Of the 40% that did develop tumor, all failed to develop detectable metastasis. The tumors were characterized as fairly self limiting, necrotic, and with poor angiogenesis. In contrast to the groups receiving SW620 alone (Table 3, "SW620") or SW620 plus hybridoma cells secreting an isotype control mAb (Table 3, "SW620 +control mAb"), all mice injected with SW620 and hybridoma cells secreting IgG1 anti-sTn antibody (Table 3, "SW620 +anti-sTn mAb") developed large tumors, and also developed significant liver and spleen metastasis. The tumors were characterized as highly invasive, and with notable angiogenesis. These results further confirm that anti-shed tumor antigen antibody (e.g., anti-sTn-mucin antibody), in the presence of shed tumor antigen (e.g., mucin) produced by tumor cells, can highly promote tumor progression (growth, invasion, and metastasis). Plasma cells, progeny of shed tumor antigen-specific B cells, produce the that anti-shed tumor antigen antibody. Hence, tolerizing of shed tumor antigen-specific B cells, by the methods and a therapeutically effective amount of the composition according to the present invention, can reduce the number of plasma cells that can be produced therefrom which secrete anti-shed tumor antigen antibody; and hence, reduce their participation in promoting tumor progression.

TABLE 3

| Cells | % reject Tumor | Tumor necrosis | Angio-genesis | Metasta-sis | shed mucin |
|---|---|---|---|---|---|
| SW620 | 20% | massive | 1.3 | negative | positive |
| SW620 + control | 60% | massive | 0.3 | negative | positive |
| SW620 + anti-sTn mAb | 0% | scarce | 14.6 | liver + spleen | positive |

Figure 7:
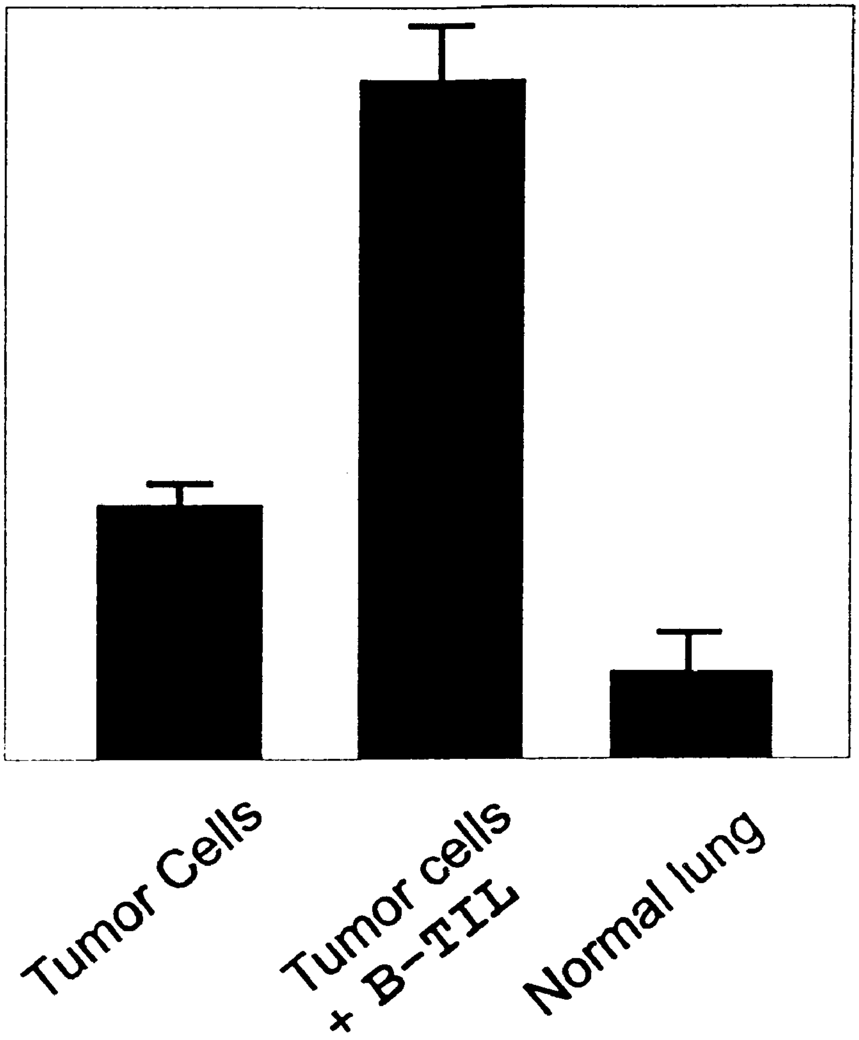
FIG. 7 is a bar graph illustrating the comparison of lung metastasis in athymic nude mice injected with tumor cells alone, with tumor cells and B-TIL, or with saline.

1.7 B Cells can promote Tumor Progression in absence of a T Cell Intermediary Response This Example relates to determining whether B cells which comprise a subpopulation of shed tumor antigen specific B cells (e.g., B-TIL) alone can promote metastasis via a direct action by the B cells, or whether a host T cell is required. In this illustration, athymic nude mice (nu/nu 3CH) were used because these mice lack functional T lymphocytes, but are B lymphocyte-competent. B-TIL were assessed for their ability to influence the progression of metastasis in athymic nude mice. Tumor from tumor bearing mice (C3H mice injected with Met 129 tumor cells in the mammary pad) were used as a source to isolate B-TIL. Isogeneic athymic nude mice were then injected via the tail vein with either Met 129 tumor cells alone, with Met 129 tumor cells and B-TIL, or with saline (normal control). Fourteen days postinjection, lung metastasis were assessed by removing, drying, and weighing the lungs of the injected athymic nude mice. As shown in FIG. 7, injections of B-TIL with tumor cells greatly promoted lung metastasis ("Tumor cells +B-TIL), as compared to tumor cells alone ("Tumor cells") and the control ("Normal lung"). The promotion of lung metastasis observed in these T cell deficient, B cell competent mice was statistically significant; and is further evidence that B cells can promote metastasis independent of a host T cell intermediary response.

EXAMPLE 2

The evidence presented in Example 1 illustrates that shed antigen may comprise repeated, antigenic carbohydrate determinants which are capable of being immunostimulatory in inducing a humoral immune response that results in the production of anti-shed antigen antibody; that this anti-shed antigen antibody can complex to shed antigen in forming immune complexes; that such immune complexes may be immunostimulatory by having a threshold level for spacing, and number of antibody molecules, necessary for receptor (FcγRI) crosslinking on immune effector cells and other receptor-bearing cells; and that one or more biological effects, induced by such cross-linking, can act to promote disease progression. From these results, it is clear that there can be a chronic activation of B cells to the repeated, antigenic carbohydrate determinant of shed antigen. In that regard, shed antigen can be presented to newly recruited (naive) B cells which may result in the activation of such B cells to become shed antigen-specific B cells; wherein shed antigen presentation may comprise one or more of shed antigen alone, or in a form as presented by one or more types of antigen presenting cells (e.g., follicular dendritic cell, or a B cell). Hence, shed antigen-specific B cells have, as part of their surface Ig, an idiotype (a) that can generally be distinguished from idiotypes present on B cells not activated by shed antigen, and (b) that bind to shed antigen via a repeated, antigenic carbohydrate determinant. Shed antigen-specific B cells displaying such idiotypes are the B cells targeted to be tolerized with a therapeutically effective amount of a composition according to the present invention containing a suppressive amount of the repeated, antigenic carbohydrate determinants.

In one embodiment according to the present invention, provided are compositions for use in tolerizing shed tumor antigen-specific B cells present in a pro-tumor immune response. In this embodiment, the composition is produced such that when it contacts and interacts with shed tumor antigen-specific B cells, the B cells are then induced to tolerance. Additionally, the composition may compete with shed tumor antigen for anti-shed tumor antigen antibody, thereby reducing formation of immunostimulatory immune complexes containing shed tumor antigen. A composition according to the present invention comprises a substantially non-immunogenic carrier molecule linked to a plurality of a repeated, antigenic carbohydrate determinant in a manner such that the spacing between each molecule of the determinant, and the number, size (e.g., length), and density of the determinant are appropriate to form a composition that is suppressive with respect to shed tumor antigen-specific B cells displaying an idiotype that binds to such determinant. Such spacing, size, number, and density can be determined by one skilled in the art using methods described previously (see, e.g., U.S. Pat. No. 5,126,131, and U.S. Pat. No. 5,276,013). For shed tumor antigen, the repeated, antigenic carbohydrate determinant, linked in multiple numbers to the substantially non-immunogenic carrier molecule, may be in the form of a carbohydrate chain with an end group capable of being linked to the carrier molecule. The carbohydrate chain may be derived from the shed tumor antigen; e.g., sheared or enzymatically cut, and purified from the shed tumor antigen (see, e.g., Nakada et al., 1993, *Proc. Natl. Acad. Sci. USA* 90:2495–2499) or synthesized (e.g., chemically, enzymatically, or recombinantly) using methods known to those skilled in the art (see, e.g., Iijima and Ogawa, 1989, *Carbohydrate Res.* 186:95–106; U.S. Pat. No. 4,935, 503) based on information about its chemical nature from the shed tumor antigen. In a preferred embodiment, the composition has a molecular mass which is less than 100, 000 daltons. In a more preferred embodiment, the composition is less than 100,000 daltons, and the density of the repeated, antigenic carbohydrate determinant is a threshold number to be tolerogenic; and in a more preferred embodiment, is or approaches, a maximal number of carbohydrate chains containing the determinant that can be linked to the substantially non-immunogenic carrier molecule to induce tolerance when it is in a therapeutically effective amount which contacts and interacts with shed antigen-specific B cells.

For example, and for illustration purposes, where the shed antigen is a shed tumor antigen comprising mucin, a plurality of the carbohydrate chain of NeuAcα→6GalNAcα1→ are linked to a substantially non-immunogenic carrier molecule in forming the composition according to the present invention. This composition displays a repeated, antigenic carbohydrate determinant comprising sTn, and is capable of displaying a repeated, antigenic carbohydrate determinant comprising the Tn (comprising the GalNAc portion). A moiety may be used to link the carbohydrate chain (and may or may not be part of the carbohydrate chain) or the repeated antigenic carbohydrate determinant to the substantially non-immunogenic carrier molecule. The moiety may include, but is not limited to, an amino acid, chemical group, linker, "X", and the like. In continuing this illustrative example, linked to the substantially non-immunogenic carrier molecule are a suppressive number of the carbohydrate chain comprising one or more of NeuAcα2→6GalNAcα1→O-Ser-, or NeuAcα2→6GalNAcα1→O-Thr, or NeuAcα2→6GalNAcα1→O—X, wherein the amino acids serine or threonine, or the functionally equivalent molecule ("X"), can be used to link the carbohydrate chains to the carrier molecule. "X" may substitute the function of Ser or Thr in linking the chain to the carrier without substantially affecting the function of the chain to present the repeated, antigenic carbohydrate determinant; and, as apparent to those skilled in the art, "X" may be comprise a naturally occurring amino acid other than Ser or Thr, a non-naturally occurring amino acid, an amino acid analog, an amino acid mimetic, a non-amino acid, or a linker group. The carbohydrate chains may be linked to the substantially non-immunogenic carrier molecule as single chains spaced apart in density and number to be suppressive. Alternatively, it is known that some antibodies against Tn recognize Tn in clusters; and some antibodies against sTn recognize sTn in clusters (Zhang et al., 1995, *Cancer Res.* 55:3364–3368). Thus, in another embodiment, and to bind the idiotype of sTn antigen-specific B cells with the composition according to the present invention in efforts to tolerize such B cells, the sTn containing-carbohydrate chains may be linked to the substantially non-immunogenic carrier molecule in a cluster of 2 to 3 chains, wherein such clusters are spaced apart in density and number to be suppressive. Similarly, carbohydrate chains displaying Tn (or other repeated, antigenic carbohydrate determinant of a shed antigen) may be linked to the substantially non-immunogenic carrier molecule in a cluster of 2 to 3 chains, wherein such clusters are spaced apart in density and number to be suppressive.

In another embodiment in which the shed antigen is a shed tumor antigen comprising mucin, a plurality of the carbohydrate chain GalNAcα1→ is linked to a substantially non-immunogenic carrier molecule in forming the composition according to the present invention; e.g., a suppressive amount of the carbohydrate chain comprising one or more of GalNAcα1→O-Ser-, or GalNAcα1→O-Thr, or GalNAcα1→O—X. As mentioned previously, the GalNAc containing-chains may be arranged in a clusters, wherein such clusters are spaced apart in density and number to be suppressive. In another embodiment, the shed antigen is a shed tumor antigen containing a repeated, antigenic carbohydrate determinant comprising sialic acid other than the sTn antigen. For example, a plurality of a carbohydrate chain selected from the group consisting of NeuAcα2→6Gal-, or NeuAcα2→3Gal-, or NeuAcα2→3GalNAc-, or a combination thereof, is linked to a substantially non-immunogenic carrier molecule in forming the composition according to the present invention; e.g., a suppressive amount of the carbohydrate chain comprising one or more of NeuAcα2→6Gal→-O-Ser, NeuAcα2→6Gal→O-Thr, NeuAcα2→6Gal→O—X, NeuAcα2→3Gal→-O-Ser, NeuAcα2→3Gal→O-Thr, NeuAcα2→3Gal→O—X, NeuAcα2→3GalNAc→-O-Ser, NeuAcα2→3GalNAc→-O-Thr, or NeuAcα2→3GalNAc→O—X. If desired, the NeuAc containing-chains may be arranged in a clusters, wherein such clusters are spaced apart in density and number to be suppressive.

In another embodiment in which the shed antigen is a shed leishmanial antigen comprising lipophosphoglycan, a plurality of the carbohydrate chain of galactose and mannose (e.g., Galβ1-4Man-), or $PO_4$-6(Galβ1-3)Galβ1-4Man-, is linked to a substantially non-immunogenic carrier molecule in forming the composition according to the present invention; e.g., a suppressive amount of the carbohydrate chain comprising Galβ1-4Man-, or $PO_4$-6 (Galβ1-3)Galβ1-4Man-, For example, a plurality of a carbohydrate chain selected from the group consisting of Galβ1-4Man-, $PO_4$-6(Galβ1-3) Galβ1-4Man-, or a combination thereof, is linked to a substantially non-immunogenic carrier molecule in forming the composition according to the present invention; e.g., a suppressive amount of the carbohydrate chain comprising one or more of Galβ1-4Man-Ser, Galβ1-4Man-Thr, Galβ1-4Man-X, $PO_4$-6 (Galβ1-3) Galβ1-4Man-Ser, $PO_4$-6 (Galβ1-3) Galβ1-4Man-Thr, or $PO_{4-}$ 6(Galβ1-3) Galβ1-4Man-X. If desired, the carbohydrate chains may be arranged in a clusters, wherein such clusters are spaced apart in density and number to be suppressive.

In an alternative embodiment, a cocktail (a mixture) of different compositions (differing in the species of the repeated, antigenic carbohydrate determinant presented in a suppressive amount) may be necessary to induce a tolerance effective in reducing disease progression, as it is possible that more than one species of repeated, antigenic carbohydrate determinant as presented by shed antigen may contribute to the induction of the disease progression. For example, wherein a pro-tumor immune response induced by shed tumor mucin is desired to be suppressed, a mixture of a first composition containing a suppressive amount of the carbohydrate chain NeuAcα2→6GalNAcαa1- linked to a substantially non-immunogenic carrier molecule, and a second composition containing a suppressive amount of the carbohydrate chain 6GalNAcα1-linked to a substantially non-immunogenic carrier molecule, may be administered in a therapeutically effective amount to an individual.

A method of making a composition for use in tolerizing shed antigen-specific B cells comprises linking a suppressive amount of a repeated, antigenic carbohydrate determinant to a substantially non-immunogenic carrier molecule. The method may further comprise the repeated, antigenic carbohydrate determinants being in the form of carbohydrate chains which are then linked to the substantially non-immunogenic carrier molecule. The repeated, antigenic carbohydrate determinants, or carbohydrate chains comprising the determinants, are linked to the substantially non-immunogenic carrier molecule in manner that allows the determinants to be accessible for contacting shed antigen-specific B cells when introduced in the presence of such B cells. The method may further comprise selecting, from the process of linking the repeated, antigenic carbohydrate determinant to the substantially non-immunogenic carrier molecule, a desired size (e.g., molecular mass) or size range of the composition. Such selection can be performed by any one of the methods known to those skilled in the art for separating molecules by size and/or charge. Such methods include, but are not limited to, gel filtration, size exclusion, chromatography, solubility differences, and gradient density. In a preferred embodiment, the desired size or size range of the composition is less than 100,000 daltons.

As appreciated by those skilled in the art, the molecular size of the composition according to the present invention will vary depending on factors such as the suppressive amount, and nature (e.g., length and branching) of the carbohydrate chain; the type of substantially non-immunogenic carrier molecule utilized; and the type of moiety used to link the carbohydrate chains to the carrier molecule. Depending on the type of substantially non-immunogenic carrier molecule, and the chemical nature of the carbohydrate chains to be linked thereto, there are many methods for linkage known to those skilled in the art that may be appropriately used in the linking process. Various bi-functional cross-linking reagents known to those skilled in the art may be suitable for this purpose. For example, a carbohydrate chain may be treated with a bi-functional cross-linking reagent, excess cross-linking reagent is removed, and then the treated carbohydrate chain is reacted with the appropriate active functional groups on the substantially non-immunogenic carrier molecule in a number and spacing to be suppressive in making the composition according to the present invention. For example, carbohydrate chains containing a carbohydrate molecule to be linked may be modified to contain a sulfhydryl-containing linker which then is conjugated to a haloacetylated carrier molecule. Also a portion of the carbohydrate chain (e.g., other than the portion comprising the repeated, antigenic carbohydrate determinant) may be oxidized to generate an aldehyde which may be reacted with amino groups of a substantially non-immunogenic carrier molecule in a process of linkage.

Suitable carrier molecules have been described previously (see, e.g., U.S. Pat. No. 5,126,131; and U.S. Pat. Nos. 5,276,013 and 5,268,454). Appropriate carrier molecules for the composition according to the present invention are stable, non-toxic, substantially non-immunogenic and pharmaceutically acceptable (e.g. bio-compatible). Such carrier molecules are known to those skilled in the art to include, but are not limited to one or more polymers such as polyethylene glycol, triethylene glycol, polypropylene glycol, poly-D-lysine, polyvinyl alcohol, D-EK, polyvinylpyrollidone, and a polyacrylamide carrier; and non-polymeric carbon-based carrier molecules with a predetermined number of branching groups (see, U.S. Pat. No. 5,633,395), and derivatized 2,2'-ethylenedioxydiethylamine. In making a composition according to the present invention, it is preferred that the composition not have an excessively large molecular size as such large molecules with repeated, antigenic carbohydrate determinants may become T-independent antigens which can ultimately induce an antibody producing response (e.g., differentiation of shed antigen-specific B cells into plasma cells that secrete anti-shed antigen antibody), rather than effecting tolerization of such B cells. Thus, in a preferred embodiment, a composition according to the present invention may be a molecular mass (“molecular size”) in the range of from about 200 daltons to about 200,000 daltons; and in a more preferred embodiment a composition according to the present invention may be a molecular size in the range of from about 20,000 daltons to less than 100,000 daltons.

The composition may be screened for binding activity and suppressive activity using any one of a number of in vitro or in vivo assays. For example, binding activity of the composition to anti-shed antigen antibody (that has binding specificity for the repeated, antigenic carbohydrate determinant in the composition) can be measured by an immunoassay such as an enzyme-linked immunosorbent assay (ELISA), or radioimmunoassay. Thus, using mucin as an exemplary shed tumor antigen for illustration purposes, the composition may be immobilized to a solid phase. Anti-mucin antibody, having binding specificity for the repeated antigenic carbohydrate determinant presented as part of the composition, is labeled with a detectable moiety and contacted with the immobilized composition; and the amount of antibody specifically bound to the composition is then detected and determined. Suppressive activity can be assessed by an in vitro assay, or an in vivo experiment using a standard animal model (see, e.g., Example 1 herein). For example, shed antigen-specific B cells (bearing surface immunoglobulin having binding specificity for the repeated, antigenic carbohydrate determinant in the composition) are contacted with a therapeutically effective amount of the composition; binding is detected; and any one or more of the following processes is observed or measured using parameters specific for the appropriate assay using methods known to those skilled in the art: (a) B cell surface immunoglobulins become crosslinked, thereby inducing apoptotic death or cytolysis of such B cells; (b) shed antigen is added to the shed antigen-specific B cells, previously treated with a therapeutically effective amount of the composition, and the shed antigen is blocked from interacting with the treated B cells; and (c) B cells, previously treated with a therapeutically effective amount of the composition, and when subsequently contacted with shed antigen, fail to differentiate into antibody producing-plasma cells. Also, the ability of the composition to compete with shed antigen in immune complex formation can be assessed using an in vitro assay (e.g., the in vitro invasion assay utilizing matrix, as previously described herein in more detail) or an in vivo standard animal model; and also may be assessed is a comparison of the immunostimulatory ability of each type of immune complex.

The composition may further comprise (e.g., or may be formulated in) a pharmaceutically acceptable aqueous solution known in the art (e.g., saline, dextrose solution, and the like) so as to facilitate administration by injection; e.g., by an appropriate route of administration that may include, but is not limited to one or more of intravenously, subcutaneously, intramuscularly, intra-peritoneally, and into lymphatic vessels. In a method of tolerizing shed antigen-specific B cells involved in disease progression, administered to an individual is a therapeutically effective amount of the composition according to the present invention; i.e., a dose sufficient to effect a tolerization of B cells specific for the shed antigen. In a preferred embodiment of the method according to the present invention of tolerizing shed tumor antigen-specific B cells involved in a pro-tumor immune response, administered to an individual is a therapeutically effective amount of the composition according to the present invention; i.e., a dose sufficient to effect a tolerization of B cells specific for the shed tumor antigen when contacting such B cells. In a more preferred embodiment, a method of treating an individual having a pro-tumor immune response comprises administering to the individual a therapeutically effective amount of the composition according to the present invention; i.e., a dose and of a specificity sufficient to effect a tolerization shed tumor antigen-specific B cells involved in the pro-tumor immune response in that individual and/or a therapeutically effective amount sufficient to effect an tolerization also characterized by a reduction (e.g, in the amount and/or function) of immunostimulatory immune complexes in the treated individual. It will be appreciated by those skilled in the art that the particular dosage, timing, and regimen will depend on such factors as properties inherent to the composition (e.g., bioclearance, size, chemical nature, stability in vivo); the health, size, and metabolism of the individual to be treated; the extent of the humoral immune response to the shed antigen (e.g., the number and anatomical location(s) of the shed antigen-specific B cells); as well as the stage of the disease. The need for sub-sequent administrations of the composition may be determined by monitoring such parameters as a rise in anti-shed antigen antibody titer in the body fluid (e.g., serum or plasma) of the individual in a period of time following the previous administration of the composition; or the detection of the same or an increased number of shed antigen-specific B cells the individual in a period of time following the previous administration of the composition. In that regard, a subsequent dosage may be administered to reestablish tolerization of shed antigen-specific B cells in the treated individual. Thus, it may be necessary to administer repetitive doses of composition over a period of time to achieve or maintain tolerization in the treated individual.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A composition for use in tolerizing shed antigen-specific B cells, wherein the composition comprises a substantially non-immunogenic carrier molecule linked to a plurality of carbohydrate chains, wherein each carbohydrate chain comprises an antigenic carbohydrate determinant, wherein the composition comprises a suppressive amount of the antigenic carbohydrate determinant, and wherein the composition has a molecular size of less than 100,000 daltons.

2. The composition according to claim 1, wherein a plurality of carbohydrate chains are linked as clusters of chains to the substantially non-immunogenic carrier molecule, wherein the clusters of carbohydrate chains are spaced apart in density and number to comprise the suppressive amount of the antigenic carbohydrate determinant.

3. The composition according to claim 1, wherein the plurality of carbohydrate chains comprises a maximal number of carbohydrate chains that can be linked to the substantially non-immunogenic carrier molecule.

4. The composition according to claim 1, wherein the antigenic carbohydrate determinant is comprised of a chain selected from the group consisting of NeuAcα2→6GalNAcα1→, GalNAcα1→, NeuAα2→6Gal-, NeuAcα2→3Gal-, NeuAcα2→3GalNAc-, Galβ1-4Man-, and $PO_4$-6 (Galβ1-3) Galβ1-4Man-.

5. The composition according to claim 4, wherein the chain further comprises a moiety used to link the chain to the substantially non-immunogenic carrier molecule.

6. The composition according to claim 1, wherein the composition further comprises a pharmaceutical acceptable aqueous solution.

7. A method for making a composition according to claim 1, wherein the method comprises linking a substantially non-immunogenic carrier molecule to a suppressive amount of antigenic carbohydrate determinant.

8. The method of claim 7, wherein the method further comprises selecting for a desired size of the composition by separating the composition by size or charge.

9. A method of tolerizing shed antigen-specific B cells involved in disease progression in an individual, the method comprising administering to an individual a therapeutically effective amount of a composition according to claim 1.

10. The method according to claim 9, wherein the composition further comprises a pharmaceutical acceptable aqueous solution.

11. A method of treating an individual having a pro-tumor immune response comprising administering to the individual a therapeutically effective amount of the composition according to claim 1.

12. The method according to claim 11, wherein the suppressive amount of the antigenic carbohydrate determinant is linked by use of a moiety to the substantially non-immunogenic carrier molecule.

13. The method according to claim 11, wherein the antigenic carbohydrate determinant of the composition is derived from a shed tumor antigen.

14. The method according to claim 11, wherein the composition further comprises a pharmaceutical acceptable aqueous solution.

15. The method according to claim 12, wherein the composition further comprises a pharmaceutical acceptable aqueous solution.

16. The method according to claim 13, wherein the composition further comprises a pharmaceutical acceptable aqueous solution.

17. The method according to claim 11, wherein the therapeutically effective amount of the composition effects tolerization in the treated individual by a process selected from the group consisting of tolerization of shed tumor antigen-specific B cells involved in the pro-tumor immune response, tolerization characterized by a reduction of immunostimulatory immune complexes, and a combination thereof.

18. The method according to claim 12, wherein the therapeutically effective amount of the composition effects tolerization in the treated individual by a process selected from the group consisting of tolerization of shed tumor antigen-specific B cells involved in the pro-tumor immune response, tolerization characterized by a reduction of immunostimulatory immune complexes, and a combination thereof.

19. The method according to claim 13, wherein the therapeutically effective amount of the composition effects tolerization in the treated individual by a process selected from the group consisting of tolerization of shed tumor antigen-specific B cells involved in the pro-tumor immune response, tolerization characterized by a reduction of immunostimulatory immune complexes, and a combination thereof.

20. A method of treating an individual having a pro-tumor immune response comprising administering to the individual a therapeutically effective amount of the composition according to claim 2.

21. The method according to claim 20, wherein the suppressive amount of the antigenic carbohydrate determinant is linked by use of a moiety to the substantially non-immunogenic carrier molecule.

22. The method according to claim 20, wherein the antigenic carbohydrate determinant of the composition is derived from a shed tumor antigen.

23. The method according to claim 20, wherein the therapeutically effective amount of the composition effects tolerization in the treated individual by a process selected from the group consisting of tolerization of shed tumor antigen-specific B cells involved in the pro-tumor immune response, tolerization characterized by a reduction of immunostimulatory immune complexes, and a combination thereof.

* * * * *